(12) United States Patent
Wilfinger

(10) Patent No.: US 8,190,269 B2
(45) Date of Patent: May 29, 2012

(54) BIOLOGICAL ELECTRODE WITH THERMOPLASTIC LAYER CONSTRUCTION

(75) Inventor: Markus Wilfinger, Rum (AT)

(73) Assignee: Leonh.Lang, Innsbruck (AT)

( * ) Notice: Subject to any disclaimer, the term of this patent is extended or adjusted under 35 U.S.C. 154(b) by 378 days.

(21) Appl. No.: 12/634,780

(22) Filed: Dec. 10, 2009

(65) Prior Publication Data

US 2010/0152827 A1 Jun. 17, 2010

(30) Foreign Application Priority Data

Dec. 12, 2008 (AT) .................................... 1934/2008

(51) Int. Cl.
*A61N 1/05* (2006.01)
(52) U.S. Cl. ........ 607/115; 607/142; 607/152; 600/391; 600/395; 600/396
(58) Field of Classification Search .................. 600/391, 600/392; 607/142
See application file for complete search history.

(56) References Cited

U.S. PATENT DOCUMENTS

| | | | | |
|---|---|---|---|---|
| 3,547,105 | A | * | 12/1970 | Ramme .......................... 600/396 |
| 4,243,051 | A | * | 1/1981 | Wittemann .................... 607/152 |
| 5,002,792 | A | * | 3/1991 | Vegoe ........................... 427/2.12 |
| 5,265,579 | A | * | 11/1993 | Ferrari .......................... 600/385 |
| 5,400,782 | A | * | 3/1995 | Beaubiah ...................... 600/394 |
| 5,785,040 | A | | 7/1998 | Axelgaard |
| 7,697,997 | B2 | * | 4/2010 | Hyatt et al. .................... 607/142 |
| 7,742,828 | B2 | * | 6/2010 | Gadsby et al. ................ 607/142 |
| 2005/0015134 | A1 | | 1/2005 | Carim |

FOREIGN PATENT DOCUMENTS

| | | |
|---|---|---|
| EP | 0097436 A1 | 1/1984 |
| EP | 0778046 A2 | 6/1997 |
| EP | 1905479 A1 | 4/2008 |
| WO | WO 98/41278 A1 | 9/1998 |

OTHER PUBLICATIONS

Anonymous: "Typical Properties for 3M Electrically Conductive Adhesive Films", 3M Technical Bulletin, Online, Feb. 2000, pp. 1-4. XP002572097, URL: http://multimedia.3m.com.
European Search Report of corresponding European application No. EP 09015126 dated Mar. 15, 2010.

* cited by examiner

*Primary Examiner* — Kennedy Schaetzle
(74) *Attorney, Agent, or Firm* — Rissman Hendricks & Oliverio LLP

(57) ABSTRACT

A bioelectrode comprising a skin-side, electrically conducting adhesive layer (7) and a flexible electrical connecting cable (4) which in an electrically insulating cable sheath (5) includes at least one electrical conductor (6), preferably in the form of a braid comprising a plurality of individual wires or conducting individual fibers, wherein the electrode-side end (4a) of the connecting cable (4) is arranged between two thermoplastic layers (2, 3) which are welded together at least region-wise, wherein both thermoplastic layers (2, 3) are electrically conducting and are electrically connected to the electrical conductor (6) of the connecting cable (4).

16 Claims, 6 Drawing Sheets

BIOLOGICAL ELECTRODE WITH THERMOPLASTIC LAYER CONSTRUCTION

FIELD OF THE INVENTION

A bioelectrode comprising a skin-side, electrically conducting adhesive layer and a flexible electrical connecting cable which in an electrically insulating cable sheath includes at least one electrical conductor, preferably in the form of a braid comprising a plurality of individual wires or conducting individual fibers.

BACKGROUND OF THE INVENTION

Bioelectrodes are used in many ways. Either current is fed to the human or animal body as in the case of a defibrillation electrode or stimulation electrode or current is carried off from the body (for example neutral electrodes or measurement electrodes).

SUMMARY OF THE INVENTION

The object of the invention is to provide a bioelectrode in which the electrical connecting cable has a good mechanical hold in the electrode and also good electrical contact is ensured in relation to those layers of the electrode, which finally feed the current to the skin or take it therefrom.

According to the invention the object is achieved in that the electrode-side end of the connecting cable is arranged between two thermoplastic layers which are welded together at least region-wise, wherein both thermoplastic layers are electrically conducting and are electrically connected to the electrical conductor of the connecting cable.

The fact of bonding the electrode-side connecting end between two thermoplastic layers, in accordance with the invention, makes it possible on the one hand to achieve a good mechanical hold and at the same time to provide an excellent electrical connection to the two thermoplastic layers which are electrically conducting.

The electrically conducting thermoplastic layers make it possible for the current which is supplied by way of the electrical connecting cable to be uniformly distributed over a larger area or taken off from a larger area. It is however also possible for a specific resistance profile to be incorporated in the electrically conducting thermoplastic layer which can also comprise a plurality of sublayers, for example in such a way that the surface resistance decreases or increases as desired from the central connecting point of the electrode-side cable end to the edge of the electrically conducting thermoplastic layer. At any event a specifically targeted current distribution in relation to an area is possible.

The two thermoplastic layers can be welded together with the inclusion of (by including) the electrode-side connecting cable between the two layers for example thermally or by means of ultrasound.

Further advantages and details of the invention are set forth more fully with reference to the specific description hereinafter.

DETAILED DESCRIPTION OF THE INVENTION

Figure 1A:
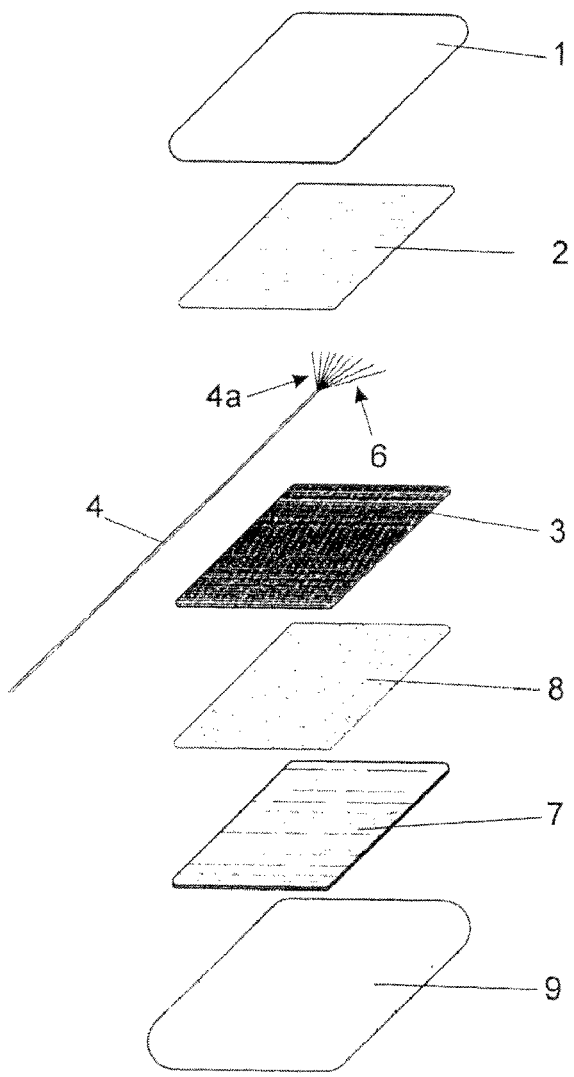
FIG. 1a shows a first embodiment by way of example of the invention as a diagrammatic exploded view.
Figure 1B:
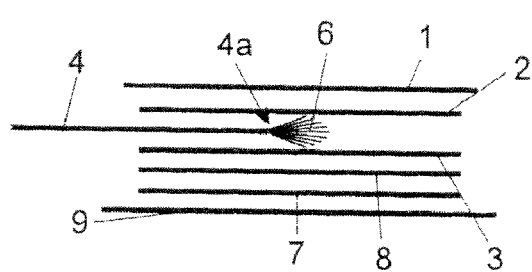
FIG. 1b shows the FIG. 1a electrode as a diagrammatic cross-sectional view.

FIGS. 1a and 1b show a first embodiment by way of example of an electrode according to the invention, in particular a defibrillation electrode.

The electrode in FIGS. 1a and 1b has beneath a carrier material 1 (for example foam material comprising polyethylene or similar, a film comprising polyethylene terephthalate or the like) two thermoplastic layers 2, 3 of which at least the lower layer 3 (that is to say the layer which is at the skin side) is electrically conducting. The thermoplastic layers 2, 3 can comprise for example: polyvinyl chloride, acrylonitrile butadiene styrene, polyurethane, polyethylene or the like. The electrical conductivity of the thermoplastic layer 3 can be achieved for example by metallic inclusions or inclusions on a carbon basis (carbon black, graphite). The electrical resistance across the electrode can be varied by suitable distribution of such inclusions or a multi-layer configuration in respect of the layer 3.

Now in accordance with the invention the electrode-side free end 4a of the connecting cable 4 is arranged between the two thermoplastic layers 2, 3 which are welded together at least region-wise. It is pointed out that the cross-sectional view in FIG. 1b only shows the layer sequence, but the individual layers of the electrode can naturally bear directly against each other and be connected to each other. In that respect the diagrammatically illustrated fan of the individual wires/individual fibers of the braid is also disposed horizontally flat, as shown in FIG. 1a. The layer 2 is intimately connected at least in region-wise relationship to the layer 3 with the inclusion of the electrode-side end 4a of the connecting cable 4. Thus the cable end 4a has a good mechanical hold in the electrode and also excellent electrical contact with the conducting thermoplastic layer 3.

Figure 1C:
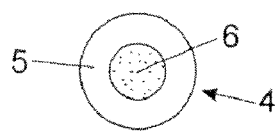
FIG. 1c shows a cable cross-section.

As shown in cross-section in FIG. 1c the electrical connecting cable 4 includes an electrically insulating cable sheath 5 in which there is at least one electrical conductor 6. Preferably that electrical conductor 6 is a braid comprising a plurality of individual wires/individual fibers.

Materials which can be used for the insulating cable sheath are polyethylene, polypropylene or polyvinyl chloride or the like. The conducting wires can be carbon fiber strands which can comprise several 1000 to several 10,000 individual fibers which can be metallised. Metal braids alone or metal braids combined with carbon fibers can also be used as conducting wires. Such a cable configuration makes it possible for the cable end to be stripped of insulation for example over a length of between 0.5 cm and 2 cm and for the individual wires of the braid then to be fanned open, as diagrammatically shown in FIGS. 1a and 1b. Such a fanning makes it possible to produce an even better mechanical and electrical contact between the electrode-side cable end 4a and the electrically conducting thermoplastic layer 3. The two thermoplastic layers 2, 3 are thermally welded together at least region-wise with the inclusion of the electrode-side free end 4a of the connecting cable 4.

With a layer thickness of the order of magnitude of between 50 and 150 micrometers in respect of the thermoplastic layers 2, 3, that welding operation can be effected at a temperature of between 150° C. and 200° C., with the application of a pressure of between about 1 N/cm$^2$ and 5 N/cm$^2$, wherein the welding duration is desirably between 5 sec and 20 sec.

Alternatively it is also possible to use an ultrasound welding method. Here an operating frequency of the order of magnitude of for example 20 KHz is suitable. The energy input is desirably between 200 Ws and 600 Ws. The pressing pressure is desirably of the order of magnitude of between 50 N/cm$^2$ and 100 N/cm$^2$. The welding times when using ultrasound welding are really short and are desirably less than a second.

In the embodiment shown in FIGS. 1a and 1b, only the lower one of the two thermoplastic layers, namely the layer 3, is electrically conducting. However the upper thermoplastic layer 2 can also be at least partially electrically conducting. That upper thermoplastic layer 2 can also replace the uppermost carrier layer 1 so that the latter can be omitted. The thermoplastic layer 2 can comprise for example acrylonitrile butadiene styrene, polyethylene, polyurethane, polyvinyl chloride or the like. If the thermoplastic layer 2 is at least partially electrically conductive it must be filled with electrically conducting filler substances, in particular pigments or fibers, or constructed like the layer 3. If the thermoplastic layer 2 is in the form of the carrier layer 1 the layer 2 may not be electrically conducting.

At the skin side the bioelectrode shown in FIGS. 1a through 1b has a conductive adhesive layer 7, preferably in the form of a conductive gel. The conductive adhesive layer which must be biocompatible can be both an adhesive hydrogel and also a conductive adhesive.

A metal layer or a metal/metal chloride layer can be arranged between the skin-side conductive adhesive layer 7 and the electrically conducting thermoplastic layer 3, the metal preferably being silver. That layer is denoted by reference 8.

Arranged beneath the conductive adhesive layer 7 is a cover material 9 which can be pulled off and which protects the conductive adhesive layer upon transport and in storage and which is pulled off prior to use. That cover material can comprise plastic materials such as polyethylene terephthalate, polystyrene, polypropylene or the like, which can also be siliconised.

Figure 2A:
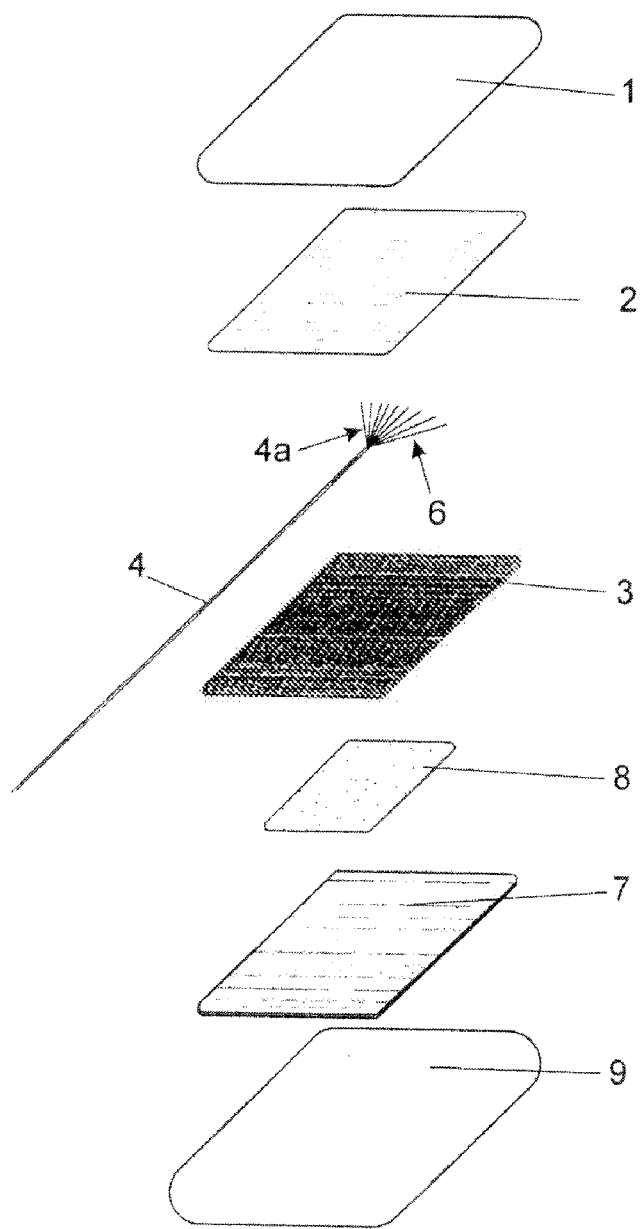
FIG. 2a shows a second embodiment by way of example of the invention as a diagrammatic exploded view and FIG. 2b shows the electrode of FIG. 2a as a diagrammatic cross-sectional view.
Figure 2B:
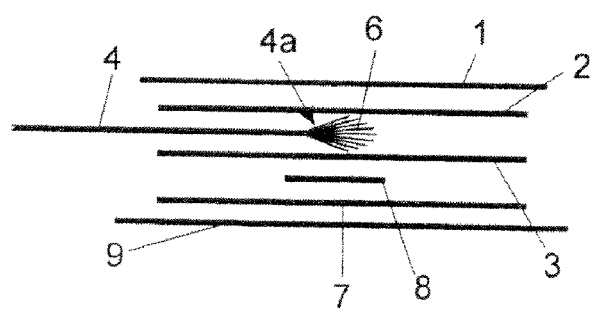

The second embodiment shown in FIGS. 2a and 2b differs from the first embodiment of FIGS. 1a and 1b substantially only in that the intermediate layer 8 (that is to say the metal layer or the metal/metal chloride layer) is of a smaller configuration in respect of area than the thermoplastic layers 2, 3 disposed thereabove.

Figure 3A:
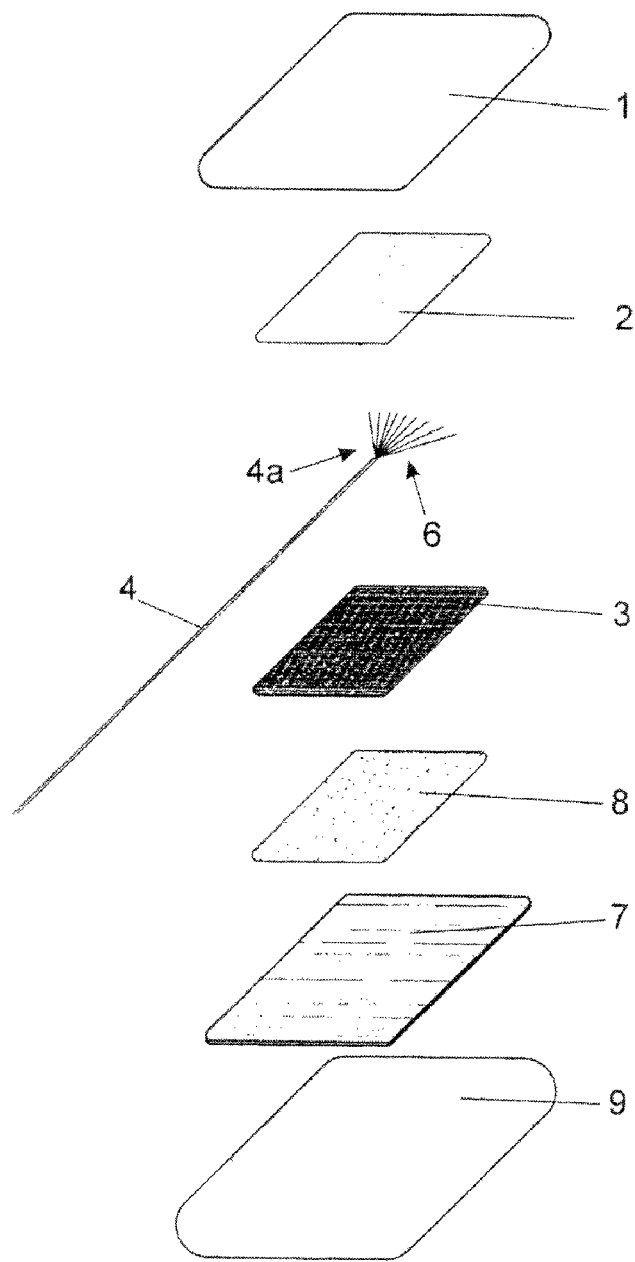
FIG. 3a shows a third embodiment by way of example of the invention as a diagrammatic exploded view and FIG. 3b shows the electrode of FIG. 3a as a diagrammatic cross-sectional view.
Figure 3B:
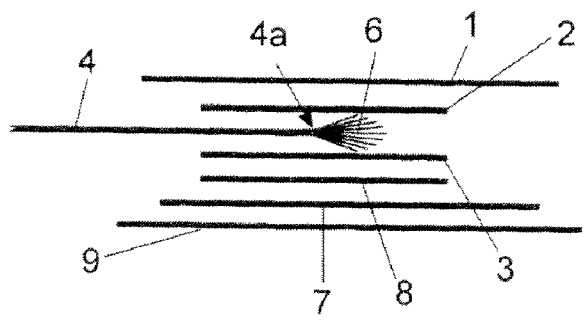

In the third embodiment of FIGS. 3a and 3b the thermoplastic layers 2, 3 are also smaller than the skin-side conductive adhesive layer 7. The cable end 4 can nonetheless be held mechanically firmly and in excellent electrical contact between the two layers 2, 3. While the lower one of the two thermoplastic layers, namely the layer 3, provides for electrical current distribution over the area, the conductive adhesive layer 7 can also enlarge that current distribution to a larger surface region.

Figure 4A:
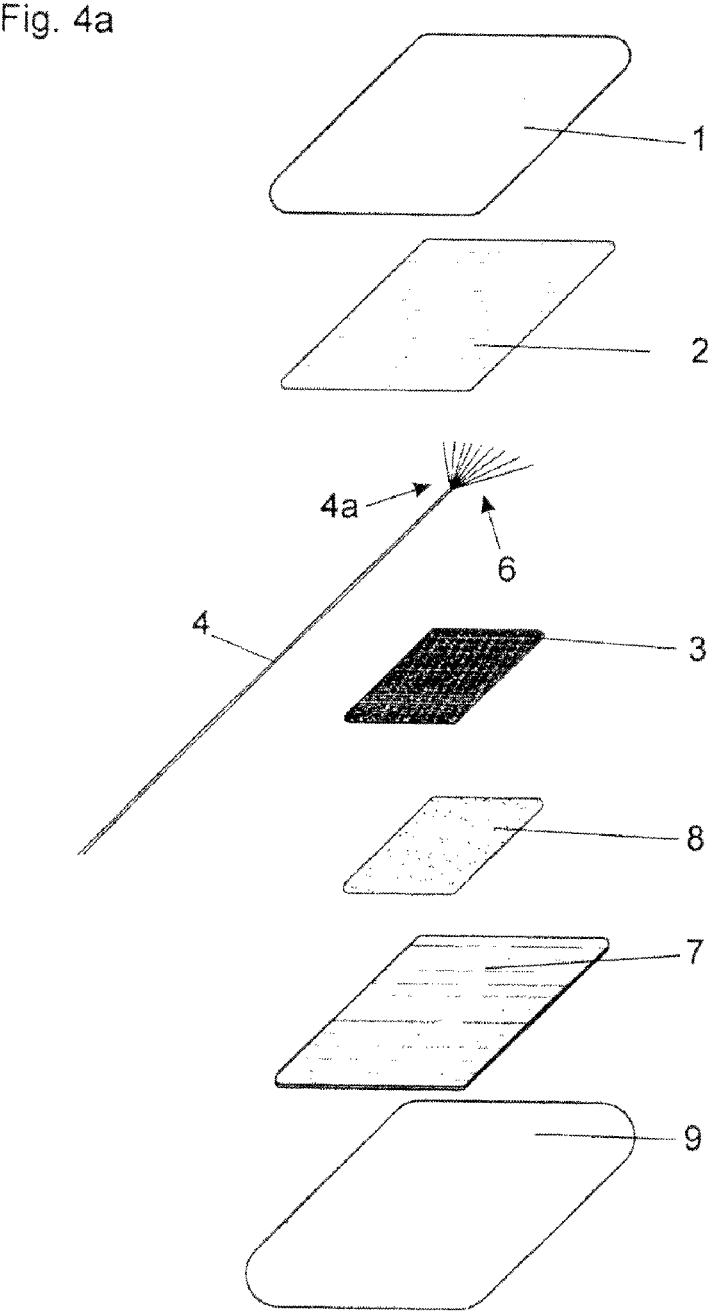
FIG. 4a shows a fourth embodiment by way of example of the invention as a diagrammatic exploded view and FIG. 4b shows the electrode of FIG. 4a as a diagrammatic cross-sectional view.
Figure 4B:
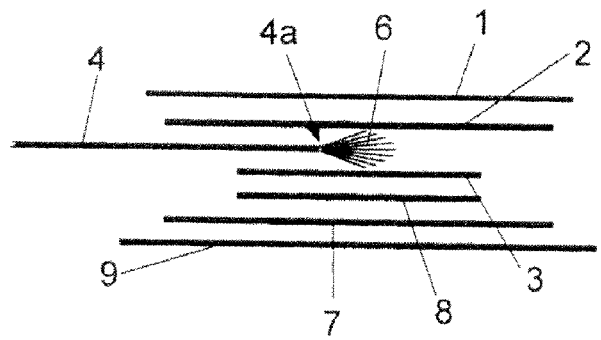

In the embodiment of FIGS. 4a and 4b, in contrast to the above-described embodiments, the two thermoplastic layers are not of the same size but are of different sizes. The upper, non-conducting thermoplastic layer 2 substantially corresponds to the rest of the size of the electrode while the lower, electrically conductive layer 3 is smaller.

The conducting metal layer is preferably a lacquer. It is preferably mixed at least with metal pigments. In addition it is possible to incorporate metal salts which with their respective metals form a constant self-potential, for example: Ag/AgCl. The metal layer can also be applied by vapor deposition.

Figure 5A:
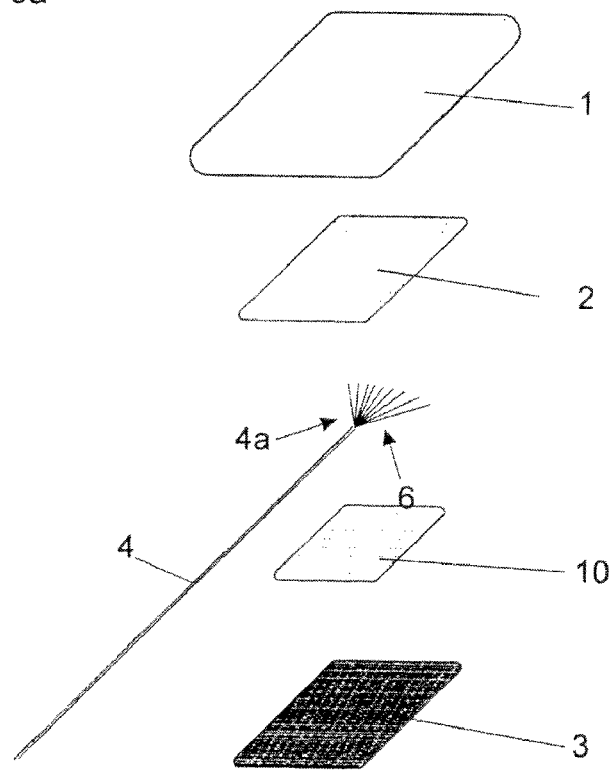
FIG. 5a shows a fifth embodiment by way of example of the invention as a diagrammatic exploded view and FIG. 5b shows the electrode of FIG. 5a as a diagrammatic cross-sectional view.
Figure 5A:
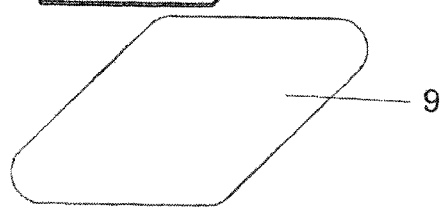
Figure 5B:
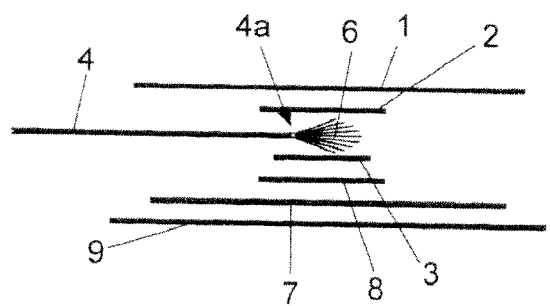

In the fifth embodiment of FIGS. 5a and 5b, there is also an additional electrically conducting, preferably metallic layer 10 between the two thermoplastic layers 2, 3 which are welded together. The area of the metallic layer 10 in this case is smaller than the area of the two thermoplastic layers 2, 3. That makes it possible for the two thermoplastic layers to be welded together in the projecting region at the periphery around the metallic layer 10. In that case the cable sheath 5 of the connecting cable 4, if of a suitable material, can also be welded to the two thermoplastic layers 2, 3. That feature can moreover also be used in the other embodiments.

It is also possible to use a film composite as the layer 10 (for example: metal/polyethylene terephthalate/sealing lacquer), wherein the insulating side is oriented at the skin side. In that case, by virtue of choosing a specific geometry for the layer 10 (for example: star-shape), the current can be optimally distributed from the layer 10, by way of the thermoplastic layer 2 to the thermoplastic layer 3, and the further electrically conducting layers, to the skin.

Figure 6A:
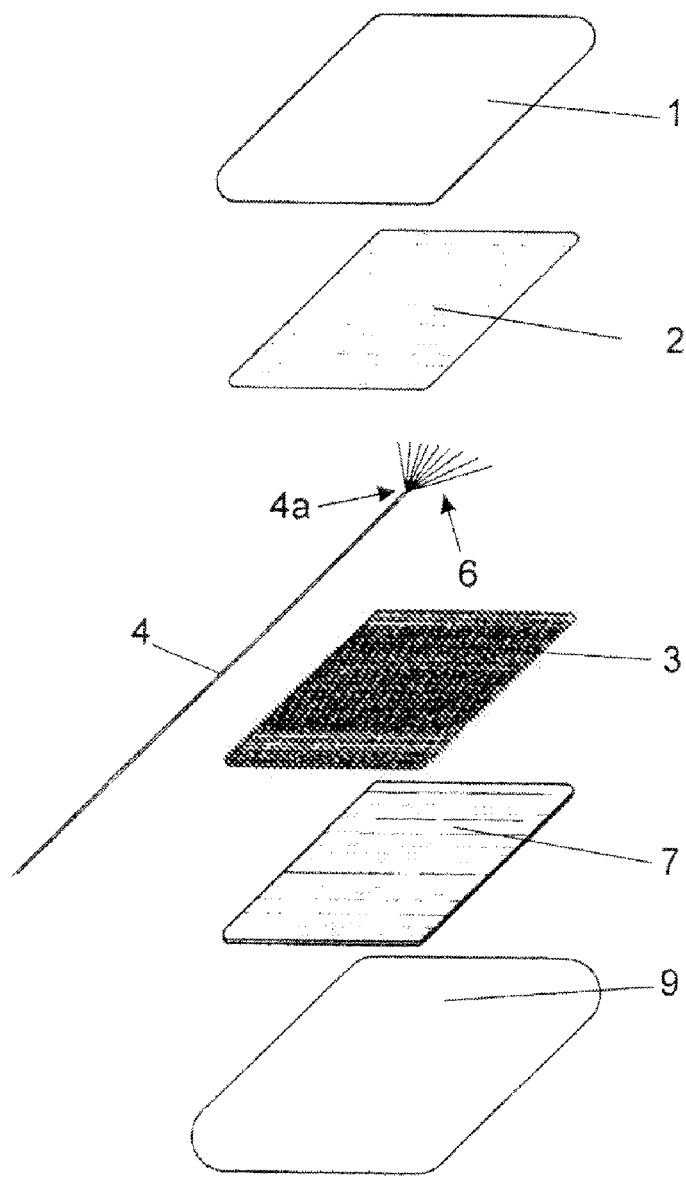
FIG. 6a shows a sixth embodiment by way of example of the invention as a diagrammatic exploded view and FIG. 6b shows the electrode of FIG. 6a as a diagrammatic cross-sectional view.
Figure 6B:
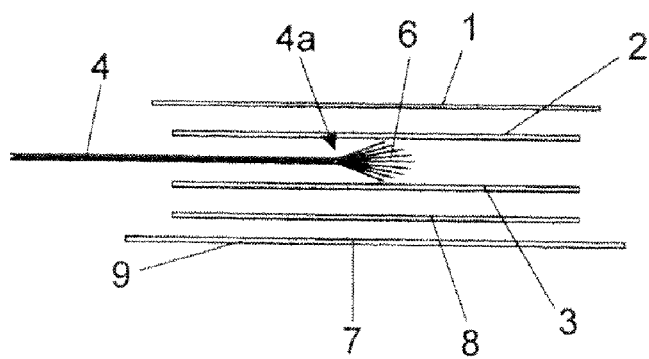

The sixth embodiment of FIGS. 6a and 6b does not have the intermediate layer 8 (metal layer or metal/metal chloride layer). That means that the skin-side conductive adhesive layer 7 directly adjoins the lower, electrically conducting thermoplastic layer 3.

It will be appreciated that the invention is not limited to the illustrated embodiments. For example the invention is suitable not only for defibrillation electrodes and electrodes which feed current to the skin (for example: stimulation electrodes) but basically also for electrodes which take current from the skin (for example neutral electrodes, measurement electrodes). The layer structure and the size relationships can differ from the illustrated embodiments. What is essential is that the electrode-side end of the connecting cable is arranged between two layers which are thermoplastically welded together so as to ensure a good mechanical hold and a good electrical connection.

The invention claimed is:

1. Bioelectrode comprising a skin-side, electrically conducting adhesive layer and a flexible electrical connecting cable which in an electrically insulating cable sheath includes at least one electrical conductor, wherein the electrode-side end of the connecting cable is arranged between two thermoplastic layers which are welded together at least region-wise, wherein both thermoplastic layers are electrically conducting and are electrically connected to the electrical conductor of the connecting cable.

2. Bioelectrode according to claim 1, wherein both thermoplastic layers are electrically conducting by metallic inclusions or carbon-based inclusions or by metallic inclusions and carbon-based inclusions.

3. Bioelectrode according to claim 1, wherein the two thermoplastic layers are thermally welded together with including there between the end of the connecting cable.

4. Bioelectrode according to claim 1, wherein the two thermoplastic layers are welded together by ultrasound with including there between the end of the connecting cable.

5. Bioelectrode according to claim 1, wherein the end of the connecting cable is stripped so that the conductor is exposed over a length preferably between 0.5 cm and 2 cm and in that stripped region has electrical contact with the electrically conducting thermoplastic layer.

6. Bioelectrode according to claim 1, wherein the at least one electrical conductor is preferably in the form of a braid comprising a plurality of individual wires or conducting individual fibers.

7. Bioelectrode according to claim 6, wherein the individual wires of the braid of the electrical connecting cable are fanned open in the region of the stripped end and lie between the two thermoplastic layers.

8. Bioelectrode according to claim 1, wherein the two thermoplastic layers are of substantially the same size.

9. Bioelectrode according to claim 1, wherein inserted between the two thermoplastic layers is an electrically conducting metallic layer which is electrically in contact with the electrical conductor of the connecting cable, wherein the two thermoplastic layers are larger than the metallic layer and are welded together in the region projecting beyond the metallic layer.

10. Bioelectrode according to claim 9, wherein the thermoplastic layers project beyond the metallic layer on all sides and are welded together in the entire peripheral region.

11. Bioelectrode according to claim 1, wherein the electrically conducting skin-side adhesive layer comprises a conductive hydrogel or electrically conducting adhesive.

12. Bioelectrode according to claim 1, wherein a metal layer or a metal/metal chloride layer is arranged between the skin-side, electrically conducting adhesive layer and the lower one of the two thermoplastic layers.

13. Bioelectrode according to claim 12, wherein the metal is silver.

14. Bioelectrode according to claim 1, wherein a cover material which can be pulled off is arranged beneath the conductive adhesive layer.

15. Bioelectrode according to claim 1, wherein an electrically non-conducting carrier material is arranged on the top side of the electrode, that is remote from the skin.

16. Bioelectrode according to claim 15, wherein the electrically non-conducting carrier material is plastic.

\* \* \* \* \*